United States Patent [19]

Kawanaka et al.

[11] Patent Number: 5,401,725
[45] Date of Patent: Mar. 28, 1995

[54] NEOVASCULARIZATION INHIBITION BY ADENOSINE-5'-PHOSPHOSULFATES

[75] Inventors: Satoshi Kawanaka; Munehiko Dombou; Hiroshi Nakajima, all of Kyoto, Japan

[73] Assignee: Unitika Ltd., Hyogo, Japan

[21] Appl. No.: 140,961

[22] Filed: Oct. 25, 1993

Related U.S. Application Data

[62] Division of Ser. No. 89,951, Jul. 12, 1993, abandoned, which is a division of Ser. No. 789,082, Nov. 7, 1991, abandoned.

[30] Foreign Application Priority Data

Nov. 8, 1990 [JP] Japan .................................. 2-305688

[51] Int. Cl.$^6$ ............................................. A61K 31/70
[52] U.S. Cl. .................................... 514/47; 536/26.2; 536/26.3
[58] Field of Search .......................................... 514/47

[56] References Cited

U.S. PATENT DOCUMENTS

| | | | |
|---|---|---|---|
| 3,701,772 | 10/1972 | Tamura et al. | 536/26.2 |
| 4,900,815 | 2/1990 | Tanaka et al. | 536/54 |
| 4,966,964 | 10/1990 | Shapiro et al. | 536/23.2 |
| 4,996,159 | 2/1991 | Glaser | 435/70.3 |
| 5,021,404 | 6/1991 | Folkman et al. | 514/26 |

OTHER PUBLICATIONS

*Sigma Chemical Company Catalog,* 1988, Sigma Chemical Company, St. Louis Mo., see p. 120.

Maione et al., "Inhibition of Angiogenesis by Recombinant Human Platelet Factor-4 and Related Peptides," *Science,* 247, 77–79 (1990).

Folkman et al., "Control of Angiogenesis with Synthetic Heparin Substitutes," *Science,* 243, 1490–1493 (1989).

Rastinejad et al., "Regulation of the Activity of a New Inhibitor of Angiogenesis by a Cancer Suppressor Gene," *Cell,* 56, 345–355 (1989).

Seydel et al. "Phosphorylation of an 85 kD Membrane Protein by a Novel Mechanism," *EMBO J.,* 7(13), 4163–4167 (1988); *Chem. Abstr.,* 110(13), p. 271, Abstr. No. 110207v (1989); only CA Abstr. supplied.

Ryu et al., "Further Characterization of Protein Sulfotransferase(s) of Rate Brain by Alkaline Hydrolysis of (List continued on next page.)

*Primary Examiner*—John W. Rollins
*Assistant Examiner*—L. Eric Crane
*Attorney, Agent, or Firm*—Wenderoth, Lind & Ponack

[57] ABSTRACT

The present invention provides, as a noval and safe vascularization inhibitor having an excellent effect, a vascularization inhibitor which is characterized by containing, as the effective ingredient, 3-phosphoadenosine 5'-phosphosulfate or adenosine 5'-phosphosulfate which is expressed by the following general formula:

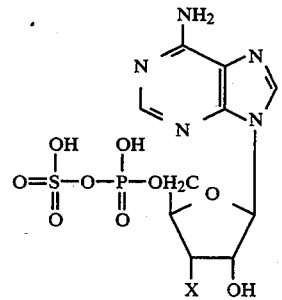

(where, x represents a phosphate or hydroxide group) or a pharmaceutically allowable salt thereof.

1 Claim, No Drawings

OTHER PUBLICATIONS

Sulfated Proteins," *Tongmul Hakhoechi*, 33(4), 468–475 (1990); *Chem. Abstr.*, 115(13), p. 428, Abstr. No. 130407s, (1991); only CA Abstr. supplied.

Renosto et al., "ATP Sulfurase from Trophosome Tissue of Rifta Pachyptila (Hydrothermal Vent Tube Worm)," *Arch. Biochim. Biophys.*, 290(1), 66–78 (1991); *Chem. Abstr.*, 115(17), p. 407, Abstr. No. 177934b, (1991); only CA Abstr. supplied.

Bicknell et al., "The Stereochemical Course of Nucleotidyl Transfer Catalyzed by ATP Sulfurase," *J. Biol. Chem.*, 257(15), 8922–8927 (1982); *Chem. Abstr.*, 97(17), p. 315, Abstr. No. 140856m, (1982); only CA Abstr. supplied.

Lee et al., "Direct Photoaffinity Labeling of Proteins with Adenosine 3'-[$^{32}$P]phosphate 5'-phosphosulfate. Atractyloside Inhibits Labeling of a $M_r$–34,000 Protein in Adrenal Medullary Golgi Fraction," *J. Biol. Chem.*, 259(17), 11153–11156 (1984); *Chem. Abstr.*, 101(23), p. 239, Abstr. No. 206261y, (1984); only CA Abstr. supplied.

Adams et al., "Preparation of Labeled Adenosine 5'–Phosphosulfate Using APS[adenosine 5'-phosphosulfate] Reductase From *Thiobacillus Dentrificans*," *Anal. Biochem.*, 42(1), 207–213 (1971); *Chem. Abstr.*, 75(7), p. 10, Abstr. No. 44845g, (1971); only CA Abstr. supplied.

Cooper et al., "Two New Reactions of the Activated Sulfates Adenylylsulfate and 3'-Phosphoadenylsulfate with Ammonia," *Zeitschrift fur Naturforschung*, 35c(1–2), 159–162 (1980).

Horwitz et al., "Studies on Bovine Adrenal Estrogen Sulfotransferase III. Facile Synthesis of 3'-Phospho- and 2'-Phosphoadenosine 5'-Phosphosulfate," *Biochim. Biophys. Acta*, 480, 376–381 (1977).

Ashino–Fuse et al., "Medroxyprogesterone Acetate, An Anti–Cancer and Anti–Angiogenic Steroid, Inhibits the Plasminogen Activator in Bovine Endothelial Cells," *Int. J. Cancer*, 44, 859–864 (1989).

Folkman et al., "Angiogenesis Inhibition and Tumor Regression Caused by Heparin or a Heparin Fragment in the Presence of Cortisone," *Science*, 221, 719–725 (1983).

NEOVASCULARIZATION INHIBITION BY ADENOSINE-5'-PHOSPHOSULFATES

This application is a Divisional of now abandoned, application Ser. No. 08/089,951, filed Jul. 12, 1993, which is a Divisional of Ser. No. 07/789,082, filed Nov. 7, 1991, now abandoned.

FIELD OF THE INVENTION

The present invention relates to a neovascularization inhibitor containing 3-phosphoadenosine 5'-phosphosulfate or adenosine 5'-phosphosulfate, which is expected to provide usefulness as a chemotherapeutic agent against malignant tumors and as a preventive or therapeutic drug against various diseases caused by vascular hyperplasia.

DESCRIPTION OF RELATED PRIOR ARTS

Progress or metastasis of malignant tumors, and such diseases as rheumatoid arthritis, diabetic retinopathy, retinopathy of prematurity, senile macular degeneration, neovascular glaucoma and hypergeneration of scars after wound healing are know to be caused by the hyperplasia of the blood vessel (particularly the peripheral capillary vessel).

As preventive or therapeutic medicines against these diseases, therefore, various neovascularization inhibitors containing, as effective ingredients, substances having an inhibitory function to neovascularization have been developed.

The neovascularization inhibitory substances reported to date include, for example, medroxyprogesterone (Ashiya, et al.: Int. J. Cancer, 1989, 44, 895), sulfated protamine (Ogawa et al: Exp. Pathol., 1986, 30, 143), combination of heparin and cortisone (J. Folkman, et al.: Science, 1983, 221, 719), prednisolone acetate (J. B. Robin: Arch. Opthalmol., 1985, 103, 284), herbimycin A (Japanese Patent Provisional Publication No. 295,509/88), peptide from retinal pigment epithelial cell (U.S. Pat. No.4,996,159), sulfated polysaccharide (U.S. Pat. No. 4,900,815), and phenol derivatives (EP-A-295,037).

These neovascularization inhibiting substances are not however completely satisfactory as preventive or therapeutic medicaments against the above-mentioned diseases because of the insufficient inhibitory effect of neovascularization in some cases or a toxic side effects in some others.

SUMMARY OF THE INVENTION

The present invention has therefore an object to provide a novel neovascularization inhibitor having a safe and excellent effect.

The present invention provides a neovascularization inhibitor which comprises, as effective ingredients, 3-phosphoadenosine 5'-phosphosulfate or adenosine 5'-phosphosulfate, as expressed by the following general formula, or a pharmaceutically acceptable salt thereof:

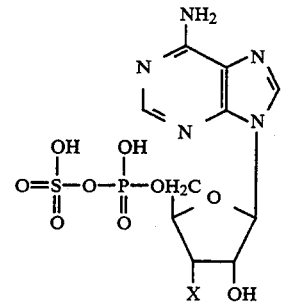

where, x represents phosphate or hydroxide group.

DETAILED DESCRIPTION OF THE INVENTION

The neovascularization inhibitor of the present invention uses, as an effective ingredient, 3-phosphoadenosine 5'-phosphosulfate (hereinafter simply referred to as "PAPS") or adenosine 5'-phosphosulfate (hereinafter simply referred to as "APS"). PAPS is a sulfate radical donor widely existing in the nature, and APS is an intermediate in PAPS biosynthesis. These sulfated adenosine nucleotides are present in an organism in a slight amount, and it is known that PAPS, for example, participates in the biosynthesis of chondroitin sulfate in the cartilage, kermatan sulfate in the skin, keratan sulfate in the cornea, heparin in the mast cells, sulphatide in the brain, and phenyl sulfate and steroid sulfate in the liver and the intestine.

It is thus well known that PAPS participates in sulfation of sugar chains or proteins, whereas no report is available regarding the neovascularization inhibitory effect of PAPS or APS. This is quite a novel function discovered for the first time by the present inventors. More particularly, PAPS and APS have an excellent function of inhibiting neovascularization as compared with the conventional neovascularization inhibitory substances, and furthermore, have a very low toxicity, these being natural products.

When preparing a neovascularization inhibitor containing PAPS or APS as an effective ingredient, commercially available enzyme-synthesized PAPS or APS may be employed. It may also be used, as required in the form of a pharmaceutically allowable salt thereof, so that the sulfo group may be an alkali salt such as potassium or sodium or an ammonium salt. These salts may easily be manufactured by a conventional process.

The neovascularization inhibitor of the present invention may be administered as an injection, an oral medicine, or a suppository, singly or in mixture with an excipient or a carrier, in accordance with the particular purpose of use. The pharmaceutical preparation may be accomplished by a conventional method: when preparing it into a solid oral medicine, for example, a binder, a disintegrator, a smoothening brightener, a coloring agent, a taste corrigent, and/or an odor corrigent are added as required to the effective ingredient such as PAPS or APS added with an excipient, and the resultant mixture is pharmaceutically prepared into tablets, pills, capsules or granules by a conventional process. When preparing it into a liquid medicine, this may be accomplished by adding a taste corrigent or a stabilizer to the effective ingredient to form a liquid agent or an injection.

The content of the effective ingredient to be blended in the thus prepared neovascularization inhibitor, varying with the purpose of use, symptoms and the form of medicament, should be within a range of from 0.01 to 100 w/w %, or more preferably, of from 0.05 to 80 w/w %.

The dose per day thereof, also depending upon the purpose of use, the frequency of administrations, the form of medicament, the symptoms, age and body weight of the administered, should be within a range of from 0.1 to 1,500 mg of the effective ingredient per kg of body weight, or more preferably, from 1 to 500 mg. The daily dosage of administration may be divided into two to four times.

Now, the present invention is described below further in detail by means of examples.

EXAMPLE 1

In accordance with the method proposed by D. H. Ausprunk, et al. (Am. J. Pathol., 1975, 97, 597), the neovascularization inhibitory effect of commercially available PAPS and APS (Sigma Corporation) was examined.

Drops of PAPS or APS of 1, 10, 100 and 1,000 μg were added on the chorio-allantoic membranes of three-day-aged fertilized eggs of fowl, and the appearance of neovascularization after the lapse of two days was observed.

The results are as shown in Table 1, in which the symbols (+), (++) and (+++) show the neovascularization inhibitory rates as compared with a control group not treated with PAPS or APS, and represent respectively 10 to 80% (+), 80 to 70% (++) and 70 to 100% (+++) (same applies also to Table 2 hereafter).

TABLE 1

| Neovascularization inhibitory substance | Dose (μg) | | | |
|---|---|---|---|---|
| | 1 | 10 | 100 | 1,000 |
| PAPS | + | ++ | ++ | +++ |
| APS | + | + | ++ | +++ |

As is clear from Table 1, both the commercially available PAPS and APS demonstrated a slight effect with a dose of administration of 10 μg, and a perfect neovascularization inhibitory effect with a dose of at least 100 μg.

EXAMPLE 2

PAPS and APS were enzyme-synthesized by using ATP sulfurirase and APS kinase derived from *Penicillium chlysogenum* curde enzyme solution.

More specifically, the *Penicillium chlysogenum* crude enzyme solution in an amount of 100 g was treated with 30 to 55%-saturated ammonium sulfate fractionation, and the resultant precipitate was dislized by means of a 50 mM tris-hydrochloric acid buffer solution (pH8.5). Then, 10 mM magnesium sulfate, 5 mM ATP magnesium and 20 units of inorganic pyrophosphatase were mixed with this buffer solution, and the mixture was caused to react for two hours at a temperature of 30° C. and then boiled. Subsequently, the supernatant thereof was passed through Dowex 1 Column and Sephadex G-10 Column, and was subjected to paper electrophoresis with Whatman 3 MM to obtain PAAS. APS was obtained by acid-decomposing this PAPS.

Then, the thus enzyme-synthesized PAPS and APS were tested for the neovascularization inhibitory effect thereof in accordance with the same procedure as in the Example 1.

The results are as shown in Table 2: the PAPS and APS obtained by enzyme-synthesis inhibited neovascularization in a dose-dependent manner within a range of dose of from 1 to 1,000 μg, similarly to those commercially available in the Example 1.

TABLE 2

| Neovascularization inhibitory substance | Dose (μg) | | | |
|---|---|---|---|---|
| | 1 | 10 | 100 | 1,000 |
| PAPS | + | ++ | ++ | +++ |
| APS | + | + | ++ | +++ |

EXAMPLE 3

In accordance with the method proposed by M. A. Gimbrone, et al. (J. Nat. Can. Inst., 1974, 52, 413), the inhibitory effect of commercially available PAPS and APS on neovascularization in the cornea of rabbits was examined.

First, the center portion of the cornea of a rabbit was incised by about 2 mm by means of a scalpel to form a spot along the corneal wall, and then, a previously prepared slow-releasing pellet containing 10 μg prostatgrandin $E_1$ or 200 μg cuprous chloride and 100 μg or 1.0 mg PAPS or APS (Sigma Corporation) in compliance with the method proposed by R. Langer, et al. (Nature, 1979, 263, 797) was inserted with fixed into this spot.

As a result, with any of the doses of 100 μg and 1.0 mg, PAPS and APS were observed to perfectly inhibit the neovascularization caused by prostatgrandine $E_1$ or cuprous chloride for seven days thereafter.

EXAMPLE 4

For a neovascularization inhibitor prepared by dissolving PAPS or APS into 50% dimethylsulfoxide, the therapeutic effect on an experimental diabetic retinopathy was investigated.

First, streptozocin in an amount of 65 mg/kg was administered to a six-week aged male wister rat from its vena caudalis, and about three months thereafter, 3,3'-iminodipropionitrile was administered. Rats in which abnormal growth of capillary vessel (hyperplasia retinitis) was observed were screened out and were subjected to a medicament administration test with ten rats as a group.

The neovascularization inhibitor in an amount of 1.5, 3.0, 4.5 or 6.0 mg/kg was administered to the rat for ten consecutive days by I.P. injections, and the extent of capillary vessel hyperplasia in vitro was observed. For comparison purposes, the effect of the medroxyprogesterone acetate (MPA), the conventional substance for inhibiting the neovascularization, was also tested by the same procedure as described above.

The results are as shown in Table 3, in which the symbol (−) represents a case where no improvement in the pathologic state was observed by the administration of the medicament as compared with rats of the control group which were administered 0.1 ml/10 g of 50% dimethylsulfoxide for ten days, and the symbols (+), (++) and (+++) indicate, respectively, improving effects of pathologic state of 10 to 30%, 30 to 70% and 70 to 100%.

As is clear from Table 3, the neovascularization inhibitor of the present invention containing PAPS or APS as the effective ingredient has a beneficial effect on the pathologic state in an amount of 10% for the 1.5 mg/kg administration group, 70% for 3.0 mg/kg group, and at least 80% for the 6.0 mg/kg group. For any of the doses, an excellent therapeutic effect was revealed as compared with the conventional neovascularization inhibitors containing MPA as the effective ingredient.

TABLE 3

| Effective ingredient of neovascularization inhibitor | Dose (mg/kg) | | | |
| --- | --- | --- | --- | --- |
|  | 1.5 | 3.0 | 4.5 | 6.0 |
| PAPS | + | ++ | +++ | +++ |
| APS | + | + | +++ | +++ |
| MPA | − | + | + | ++ |

Next, an example of experiment regarding toxicity of the neovascularization inhibitor of the present invention is described.

EXPERIMENT

Injections were prepared by dissolving PAPS or APS in an amount within a range of from 500 to 3,500 mg/kg to 50% dimethylsulfoxide, and were parenterally administered (I.V. or I.P. injection) to rats.

As a result, no cases of intoxication or lethality were observed for any of the above-mentioned doses of administration.

What is claimed is:

1. A method for the inhibition of neovascularization in a patient in need of such treatment which comprises administering to said patient an effective amount for the inhibition of neovascularization, of 3-phosphoadenosine 5'-phosphosulfate or adenosine 5-phosphosulfate which is expressed by the following formula:

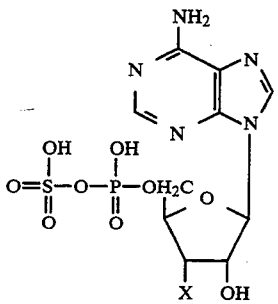

where, X represents a phosphate or hydroxide group or a pharmaceutically acceptable salt thereof.

* * * * *